(12) United States Patent
Lindstedt-Alstermark

(10) Patent No.: US 7,309,720 B2
(45) Date of Patent: Dec. 18, 2007

(54) 2-ETHOXY-3-PHENYLPROPIONIC ACID DERIVATIVES FOR THE TREATMENT OF LIPID DISORDERS

(75) Inventor: Eva-Lotte Lindstedt-Alstermark, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 108 days.

(21) Appl. No.: 10/561,168

(22) PCT Filed: Jun. 16, 2004

(86) PCT No.: PCT/GB2004/002619

§ 371 (c)(1),
(2), (4) Date: Dec. 16, 2005

(87) PCT Pub. No.: WO2004/113276

PCT Pub. Date: Dec. 29, 2004

(65) Prior Publication Data

US 2006/0178432 A1   Aug. 10, 2006

(30) Foreign Application Priority Data

Jun. 18, 2003 (GB) ................... 0314078.7

(51) Int. Cl.
*A61K 31/192* (2006.01)
(52) U.S. Cl. ............... 514/571; 562/429; 514/568; 514/570

(58) Field of Classification Search ............... 562/429; 558/44, 51, 52; 514/571, 568, 570
See application file for complete search history.

(56) References Cited

U.S. PATENT DOCUMENTS

| 6,258,850 B1 | 7/2001 | Andersson | 514/571 |
| 6,630,600 B1 | 10/2003 | Andersson et al. | 560/55 |

FOREIGN PATENT DOCUMENTS

WO    WO 99/62872    12/1999

*Primary Examiner*—Golam M. M. Shameem
(74) *Attorney, Agent, or Firm*—Morgan, Lewis & Bockius LLP

(57) ABSTRACT

A compound of formula (I) wherein T represents O, S or NR and wherein R represents a H, a $C_{1-6}$alkyl group or a phenyl $C_{1-6}$alkyl group and pharmaceutically acceptable salts thereof, processes for preparing such compounds, their the utility in treating clinical conditions including lipid disorders (dyslipidemias) whether or not associated with insulin resistance, methods for their therapeutic use and and pharmaceutical compositions containing them

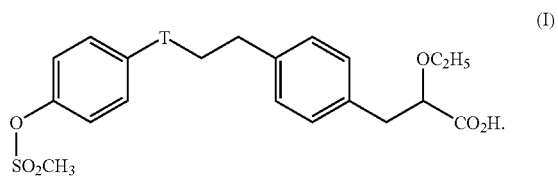

(I)

7 Claims, No Drawings

2-ETHOXY-3-PHENYLPROPIONIC ACID DERIVATIVES FOR THE TREATMENT OF LIPID DISORDERS

FIELD OF THE INVENTION

The present invention relates to certain novel 3-phenyl-2-arylalkylthiopropionic acid derivatives, to processes for preparing such compounds, to their the utility in treating clinical conditions including lipid disorders (dyslipidemias) whether or not associated with insulin resistance and other manifestations of the metabolic syndrome, to methods for their therapeutic use and to pharmaceutical compositions containing them.

BACKGROUND OF THE INVENTION

The metabolic syndrome including type 2 diabetes mellitus, refers to a cluster of manifestations including insulin resistance with accompanying hyperinsulinaemia, possibly type 2 diabetes mellitus, arterial hypertension, central (visceral) obesity, dyslipidaemia observed as deranged lipoprotein levels typically characterised by elevated VLDL (very low density lipoproteins), small dense LDL particles and reduced HDL (high density lipoprotein) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus atherosclerosis related conditions cause up to 80% of all deaths.

In clinical medicine there is awareness of the need to increase the insulin sensitivity in patients with the metabolic syndrome and thus to correct the dyslipidaemia which is considered to cause the accelerated progress of atherosclerosis. However, currently this is not a universally accepted diagnosis with well-defined pharmacotherapeutic indications.

The S-enantiomer of the compound of formula A below

A

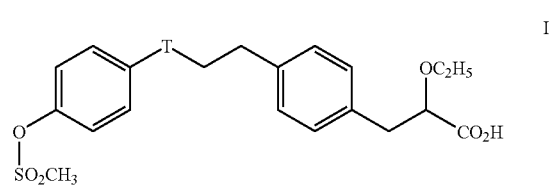

2-ethoxy-3-[4-(2-{4-methanesulfonyloxyphenyl}ethoxy) phenyl]propanoic acid, is disclosed in PCT Publication Number WO99/62872. This compound is reported to be a modulator of peroxisome proliferator-activated receptors (PPAR, for a review of the PPARs see T. M. Willson et al, J Med Chem 2000, Vol 43, 527) and has combined PPARα/PPARγ agonist activity (Structure, 2001, Vol 9, 699, P. Cronet et al). This compound is effective in treating conditions associated with insulin resistance.

Co-pending PCT application No. PCT/GB02/05743 discloses a compound of formula A

B

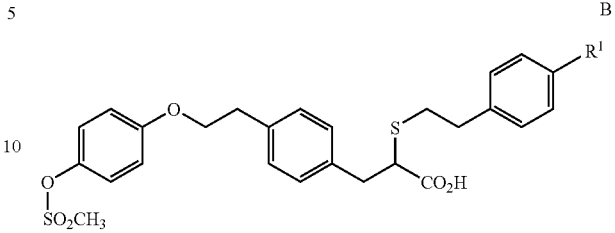

wherein $R^1$ represents chloro, fluoro or hydroxy as well as optical isomers and racemates thereof as well as pharmaceutically acceptable salts, prodrugs, solvates and crystalline forms thereof, processes for preparing such compounds, to their the utility in treating clinical conditions including lipid disorders (dyslipidemias) whether or not associated with insulin resistance, to methods for their therapeutic use and to pharmaceutical compositions containing them.

WO 02/100813 discloses that compounds of formula C

C

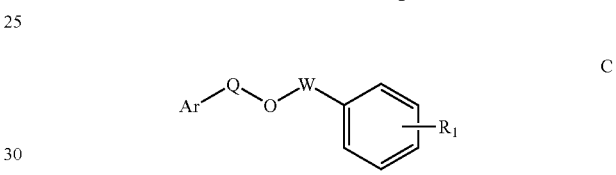

in which Ar is a substituted or unsubstituted aromatic group; Q is a covalent bond, $-CH_2-$ or $CH_2-CH_2-$; W is a substituted or unsubstituted alkylene or a substituted or unsubstituted heteroalkylene linking group from 2 to 10 atoms in length; the phenyl ring is optionally substituted with up to four substituents in addition to $R_1$ and W; and $R_1$ is inter alia $-(CH_2)_n-CH(OR_2)-(CH_2)_m E$ or $-(CH)=C(OR_2)-(CH_2)_m E$ wherein E is inter alia $COOR_3$; $R_2$ is H, an aliphatic group etc.; $R_3$ is H, an aliphatic group etc.; and n and m are independently 0, 1 or 2; are modulators of PPAR receptors.

Surprisingly a select series of compounds has now been found which are dual PPARα/PPARγ modulators.

DESCRIPTION OF THE INVENTION

The present invention provides a compound of formula I

I

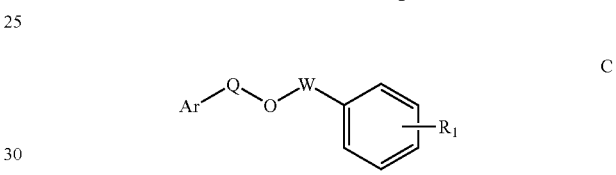

wherein T represents O, S or NR and wherein R represents a H, a $C_{1-6}$alkyl group or a phenyl $C_{1-6}$alkyl group and pharmaceutically acceptable salts thereof.

It will be appreciated by those skilled in the art the compounds of formula I contain an optically active centre and therefore can exist as enantiomers which can be separated as described later. It is expected that most, if not all, of the activity of the compounds of formula I resides in one enantiomer: either the S or the R enantiomer or the (+) or the (−) enantiomer. The enantiomers which are more active in the assays which are described later are preferred forms of the present invention. It will be understood that the present invention includes all mixtures of this active enantiomer with the other enantiomer, for example the racemic mixture, which is a useful intermediate for the active enantiomer.

The active enantiomers may be isolated by separation of racemate for example by fractional crystallization, resolution or HPLC on a chiral column (for example a Chiralpak™ AD 250×50 column). Alternatively the active enantiomers may be made by chiral synthesis from chiral starting materials under conditions which will not cause racemisation or epimerisation, or by derivatisation with a chiral reagent.

The term "prodrug" as used in this specification includes derivatives of the carboxylic acid group which are converted in a mammal, particularly a human, into the carboxylic acid group or a salt or conjugate thereof. The term "prodrug" also includes derivatives of the hydroxy substituent (when $R^1$ represents hydroxy) which are converted in a mammal, particularly a human, into the hydroxy group or a salt or conjugate thereof. It should be understood that, whilst not being bound by theory, it is believed that most of the activity associated with the prodrugs arises from the activity of the compound of formula I into which the prodrugs are converted. Prodrugs can be prepared by routine methodology well within the capabilities of someone skilled in the art. Various prodrugs of carboxy and hydroxy are known in the art. For examples of such prodrug derivatives, see:

a) Design of Prodrugs, edited by H. Bundgaard, (Elsevier, 1985) and Methods in Enzymology. 42: 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8:1-38 (1992);
d) H. Bundgaard, et al., Journal of Pharmaceutical Sciences, 77:285 (1988); and
e) N. Kakeya, et al., Chem Pharm Bull, 32:692 (1984).

The above documents a to e are herein incorporated by reference.

In vivo cleavable esters are just one type of prodrug of the parent molecule. An in vivo hydrolysable (or cleavable) ester of a compound of the formula (I) that contains a carboxy or a hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters, for example, methoxymethyl; $C_{1-6}$alkanoyloxymethyl esters, for example, pivaloyloxymethyl; phthalidyl esters; $C_{3-8}$cycloalkoxycarbonyloxy $C_{1-6}$alkyl esters, for example, 1-cyclohexyl-carbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl; and may be formed at any carboxy group in the compounds of this invention. An in vivo hydrolysable (or cleavable) ester of a compound of the formula (I) that contains a hydroxy group includes inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A specific compound of the invention is:

(2S)-2-ethoxy-3-[4-(2-{4-[(methylsulfonyl)oxy]phenoxy}ethyl)phenyl]propanoic acid and pharmaceutically acceptable salts thereof.

It will also be understood that certain compounds of the present invention may exist in solvated, for example hydrated, as well as unsolvated forms. It is to be understood that the present invention encompasses all such solvated forms. Certain compounds of the present invention may exist as tautomers. It is to be understood that the present invention encompasses all such tautomers.

Methods of Preparation

The compounds of the invention may be prepared as outlined below. However, the invention is not limited to these methods, the compounds may also be prepared as described for structurally related compounds in the prior art. The reactions can be carried out according to standard procedures or as described in the experimental section.

Compounds of formula I may be prepared by reacting a compound of formula II

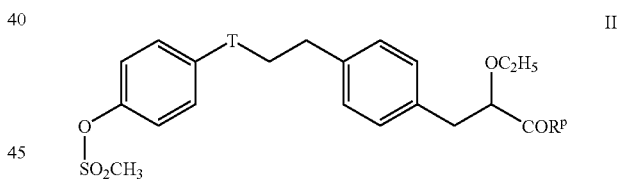

in which T is as previously defined and $R^p$ represents a protecting group for carboxylic hydroxy group as described in the standard text "Protective Groups in Organic Synthesis", $2^{nd}$ Edition (1991) by Greene and Wuts, with a deprotecting reagent. The protecting group may also be a resin, such as Wang resin or 2-chlorotrityl chloride resin. Protecting groups may be removed in accordance to techniques which are well known to those skilled in the art. One such protecting group is where $R^p$ represents $C_{1-6}$alkoxy group or an arylalkoxy group eg benzyloxy, such that $COR^2$ represents an ester. Such esters can be reacted with a a deprotecting reagent e.g. a hydrolysing agent, for example lithium hydroxide in a mixture of THF and water, at a temperature in the range of 0-100° C. to give compounds of formula I.

Compounds of formula II are believed to be novel intermediates and are claimed as another aspect of the present invention.

Compounds of formula II in which T is O may be prepared by reacting a compound of formula III

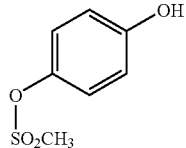

with a compound of formula IV

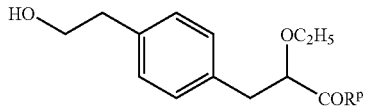

in which $R^P$ is a protected hydroxy group, for example $R^P$ is benzyloxy or ethoxy, in the presence of a coupling agent, for example cyanomethylenetri-N-butylphosphorane.

Compounds of formula II in which T is S or NR may be prepared by analogous routes or by other methods known to those skilled in the art. For example when T is NR a primary amine comprising one part of formula I may be formed and then alkylated or reductively alkylated to produce a secondary or tertiary amine of formula I as required with optional protection and deprtoection steps as appropriate.

Compounds of formula III and IV may be prepared by methods described in the Examples or by analogous methods known to those skilled in the art.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising a compound of the present invention or a pharmaceutically acceptable salt, in a pharmaceutically acceptable dosage form. Depending upon the disorder and patient to be treated and the route of administration, the compositions may be administered at varying doses.

Suitable daily doses of the compounds of the invention in therapeutical treatment of humans are about 0.0001-100 mg/kg body weight, preferably 0.001-10 mg/kg body weight.

Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or pharmaceutically acceptable derivatives thereof, in admixture with pharmaceutically acceptable adjuvants, diluents and/or carriers.

Pharmacological Properties

The present compounds of formula (I) are useful for the prophylaxis and/or treatment of clinical conditions associated with inherent or induced reduced sensitivity to insulin (insulin resistance) and associated metabolic disorders (also known as metabolic syndrome). These clinical conditions will include, but will not be limited to, general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated very low density lipoprotein (VLDL) triglyceride rich particles, high Apo B levels, low high density lipoprotein (HDL) levels associated with low apoAI particle levels and high Apo B levels in the presence of small, dense, low density lipoproteins (LDL) particles, phenotype B.

The compounds of the present invention are expected to be useful in treating patients with combined or mixed hyperlipidemias or various degrees of hypertriglyceridemias and postprandial dyslipidemia with or without other manifestations of the metabolic syndrome.

Treatment with the present compounds is expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed. Furthermore the compounds may be useful in treatment of various conditions outside the cardiovascular system whether or not associated with insulin resistance, like polycystic ovarian syndrome, obesity, cancer and states of inflammatory disease including neurodegenerative disorders such as mild cognitive impairment, Alzheimer's disease, Parkinson's disease and multiple sclerosis.

The compounds of the present invention are expected to be useful in controlling glucose levels in patients suffering from type 2 diabetes.

The present invention provides a method of treating or preventing dyslipidemias, the insulin resistance syndrome and/or metabolic disorders (as defined above) comprising the administration of a compound of formula I to a mammal (particularly a human) in need thereof.

The present invention provides a method of treating or preventing type 2 diabetes comprising the administration of an effective amount of a compound of formula I to a mammal (particularly a human) in need thereof.

In a further aspect the present invention provides the use of a compound of formula I as a medicament.

In a further aspect the present invention provides the use of a compound of formula I in the manufacture of a medicament for the treatment of insulin resistance and/or metabolic disorders.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes and obesity. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt thereof, may be administered in association with a PPAR modulating agent. PPAR modulating agents include but are not limited to a PPAR alpha and/or gamma and/or delta agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO 04/000790, WO 04/000295, WO 04/000294, WO 03/051822, WO 03/051821, WO 02/096863, WO 03/051826, WO 02/085844, WO 01/040172, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma and/or delta agonist refers to muraglitazar (BMS 298585), rivoglitazone (CS-011), netoglitazone (MCC-555), balaglitazone (DRF-2593, NN-2344), clofibrate, fenofibrate, bezafibrate, gemfibrozil, ciprofibrate, pioglitazone, rosiglitazone, AVE-0847, AVE-8134, CLX-0921, DRF-10945, DRF-4832, LY-518674, LY-818, LY-929, 641597, GW-590735, GW-677954, GW-501516, MBX-102, ONO-5129, KRP-101, R-483 (BM131258), TAK-559 or TAK-654. Particularly a PPAR alpha and/or gamma and/or delta agonist refers to tesaglitazar ((S)-2-ethoxy-3-[4-(2-{4-methanesulphonyloxyphenyl}ethoxy)phenyl]propanoic acid) and pharmaceutically acceptable salts thereof.

In addition the combination of the invention may be used in conjunction with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination. The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin, or a pharmaceutically acceptable salt, especially sodium or calcium, or a solvate thereof, or a solvate of such a salt. A particular statin is atorvastatin, or a pharmaceutically acceptable salt, solvate, solvate of such a salt or a prodrug thereof. A more particular statin is atorvastatin calcium salt. A particularly preferred statin is, however, a compound with the chemical name (E)-7-[4-(4-fluorophenyl)-6-isopropyl-2-[methyl(methylsulfonyl)-amino]-pyrimidin-5-yl](3R,5S)-3,5-dihydroxyhept-6-enoic acid, [also known as (E)-7-[4-(4-fluorophenyl)-6-isopropyl-2-[N-methyl-N-(methylsulfonyl)-amino]pyrimidin-5-yl](3R,5S)-3,5-dihydroxyhept-6-enoic acid] or a pharmaceutically acceptable salt or solvate thereof, or a solvate of such a salt. The compound (E)-7-[4-(4fluorophenyl)-6-isopropyl-2-[methyl-(methylsulfonyl)-amino]-pyrimidin-5-yl](3R,5S)-3,5-dihydroxyhept-6-enoic acid, and its calcium and sodium salts are disclosed in European Patent Application, Publication No. EP-A-0521471, and in Bioorganic and Medicinal Chemistry, (1997), 5(2), 437-444. This latter statin is now known under its generic name rosuvastatin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with a bile acid sequestering agent, for example colestipol or cholestyramine or cholestagel.

The present invention also includes a compound of the present invention in combination with an inhibitor of the ileal bile acid transport system (IBAT inhibitor).

Suitable compounds possessing IBAT inhibitory activity have been described, see for instance the compounds described in WO 93/16055, WO 94/18183, WO 94/18184, WO 94/24087, WO 96/05188, WO 96/08484, WO 96/16051, WO 97/33882, WO 98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 01/34570, WO 00/35889, WO 00/47568, WO 00/61568, WO 01/68637, WO 01/68096, WO 02/08211, WO 00/38725, WO 00/38726, WO 00/38727, WO 00/38728, WO 00/38729, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 869 121, EP 864 582, and EP 1 070 703, and the contents of these patent applications, particularly the compounds described in claim 1 and the named examples, are incorporated herein by reference.

Particular classes of IBAT inhibitors suitable for use in the present invention are benzothiepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582). Other suitable IBAT inhibitors include one of:

1,1-dioxo-3,3-dibutyl-5-phenyl-7-methylthio-8-(N-{(R)-1'-phenyl-1'-[N'-(carboxymethyl)carbamoy]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzotbiazepine;

1,1-dioxo-3-butyl-3-ethyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N'''—(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α [N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphorylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

1,1-dioxo-3,3-dibutyl-5-phenyl-7-methylthio-8-(N-{(R)-α-[N-((R)-1-carboxy-2-methylthioethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[(N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;
1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;
1,1-Dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine;
1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-2,3,4,5-tetrahydro-1,2,5-benzothiadiazepine;
1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]-4-hydroxybenzyl}carbamoylmethoxy)-2,3,4,5-tetrahydro-1,2,5-benzothiadiazepine; and
1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

According to an additional further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

a CETP (cholesteryl ester transfer protein) inhibitor, for example those referenced and described in WO 00/38725 page 7 line 22-page 10, line 17 which are incorporated herein by reference;
a cholesterol absorption antagonist for example azetidinones such as SCH 58235 and those described in U.S. Pat. No. 5,767,115 which are incorporated herein by reference;
a MTP (microsomal transfer protein) inhibitor for example those described in Science, 282, 751-54, 1998 which are incorporated herein by reference;
a nicotinic acid derivative, including slow release and combination products, for example, nicotinic acid (niacin), acipimox and niceritrol;
a phytosterol compound for example stanols;
probucol;
an omega-3 fatty acid for example Omacor™;
an anti-obesity compound for example orlistat (EP 129,748) and sibutramine (GB 2,184,122 and U.S. Pat. No. 4,929,629);
an antihypertensive compound for example an angiotensin converting enzyme (ACE) inhibitor, an angiotensin II receptor antagonist, an andrenergic blocker, an alpha andrenergic blocker, a beta andrenergic blocker for example metoprolol, a mixed alpha/beta andrenergic blocker, an andrenergic stimulant, calcium channel blocker, an AT-1 blocker, a saluretic, a diuretic or a vasodilator;
a CB1 antagonist or inverse agonist for example as described in WO01/70700 and EP 65635;
aspirin;
is a Melanin concentrating hormone (MCH) antagonist;
a PDK inhibitor; or
modulators of nuclear receptors for example LXR, FXR, RXR, and RORalpha;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula I include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula I include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

Therefore in an additional feature of the invention, there is provided a method for for the treatment of type 2 diabetes and its associated complications in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof.

According to a further aspect of the present invention there is provided a kit comprising:
a) a compound of formula I, or a pharmaceutically acceptable salt, solvate, solvate of such a salt or a prodrug thereof, in a first unit dosage form;
b) one of the other compounds described in this combination section or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula I, or a pharmaceutically acceptable salt, solvate, solvate of such a salt or a prodrug thereof, together with a pharmaceutically acceptable diluent or carrier, in a first unit dosage form;
b) one of the other compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the the treatment of metabolic syndrome or type 2 diabetes and its associated complications in a warm-blooded animal, such as man.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

EXAMPLES $^1$H NMR and $^{13}$C NMR measurements were performed on a Varian Mercury 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta scale (δ).

Unless otherwise stated, chemical shifts are given in ppm with the solvent as internal standard.

Abbreviations

DMSO dimethyl sulfoxide
EtOAc ethyl acetate
DMF N,N-dimethylformamide
THF tetrahydrofuran
MeCN acetonitrile
MeOH methanol
TFA trifluoroacetic acid
triflic trifluoroacetic
NH$_4$OAc ammonium acetate

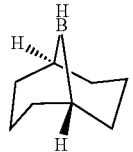

9-BBNis
t triplet
s singlet
d doublet
q quartet
m multiplet
bs broad singlet

Example 1 a) Ethyl(2S)-2-ethoxy-3-(4-{[(tifluoromethyl)sulfonyl]oxy}phenyl)propanoate

A cooled solution of triflic anhydride (1.24 g, 4.39 mmol) in CH$_2$Cl$_2$ (13 mL) was slowly added to a solution of triethylamine (0.61 g, 6.0 mmol) and ethyl(2S)-2-ethoxy-3-

(4-hydroxyphenyl)propanoate (prepared as described in WO99/62872) (0.95 g, 4.0 mmol) in $CH_2Cl_2$ (20 mL) at −40° C. under argon. The reaction mixture was stirred at −40° C. for 1.5 h and washed with cooled 0.5 M aqueous $KHSO_4$, saturated aqueous $NaHCO_3$, and brine, dried over $Na_2SO_4$ and evaporated to give the title compound as an oil (1.42 g, 96%).

$^1$H NMR (CDCl$_3$, 400 MHz): δ 1.09 (t, 3H, J=7 Hz), 1.18 (t, 3H, J=7 Hz), 2.99 (d, 1H, J=8 Hz), 3.00 (d, 1H, J=5 Hz), 3.30 (dq, 1H, J=7 and 9 Hz), 3.60 (dq, 1H, J=7 and 9 Hz), 3.97 (dd, 1H, J=5 and 8 Hz), 4.13 (q, 2H, J=7 Hz), 7.15 (dm, 2H, J=9 Hz), 7.30 (dm, 2H, J=9 Hz). $^{13}$C NMR (CDCl$_3$, 100 Mz,): δ 14.0, 14.8, 38.4, 60.8, 66.2, 79.4, 118.6 (q, J=320 Hz), 120.9, 131.1, 137.9, 148.3, 171.9 b) Ethyl(2S)-2-ethoxy-3-(4-vinylphenyl)propanoate

Tributyl(vinyl)stannane (0.98 g, 3.1 mmol) was added to a mixture of dichlorobis(triphenylphosphine)palladium(II) (95 mg, 0.13 mmol), LiCl (0.57 g, 13.5 mmol), and ethyl (2S)-2-ethoxy-3-(4-{[(trifluoromethyl)sulfonyl]oxy}phenyl)propanoate (1.00 g, 2.70 mmol) in anhydrous DMF (20 mL) under argon. The reaction mixture was heated to reflux overnight, cooled to room temperature, and poured into water. The aqueous phase was extracted with ether and the combined organic extracts were washed with water and brine, dried (MgSO$_4$) and filtered, and the solvent was removed under reduced pressure. The crude product was chromatographed over silica gel using a mixture of ethyl acetate and heptane (20:1) as the mobile phase to afford the title compound (0.45 g, 67%).

$^1$H NMR (CDCl$_3$, 400 MHz): δ 1.16 (t, 3H, J=7 Hz), 1.22 (t, 3H, J=7 Hz), 3.00 (m, 2H), 3.35 (dq, 1H, J=7 and 9 Hz), 3.60 (dq, 1H, J=7 and 9 Hz), 4.00 (dd, 1H, J=6 and 7 Hz), 4.17 (q, 2H, J=7 Hz), 5.20 (dd, 1H, J=11 and 1 Hz), 5.71 (dd, 1H, J=18 and 1 Hz), 6.69 (dd, 1H, J=18 and 11 Hz), 7.20 (dm, 2H, J=8 Hz), 7.33 (dm, 2H, J=8 Hz). $^{13}$C NMR (CDCl$_3$, 100 MHz,): δ 14.2, 15.0, 39.0, 60.8, 66.2, 80.1, 113.3, 126.1, 129.5, 135.9, 136.6, 136.9, 172.4.

c) Ethyl(2S)-2-ethoxy-3-[4-(2-hydroxyethyl)phenyl]propanoate

9-BBN (3.0 mmol, 6 mL of a 0.5 M solution in hexanes) was added to a stirred solution of ethyl(2S)-2-ethoxy-3-(4-vinylphenyl)propanoate (0.37 g, 1.48 mmol) in dry THF under argon. The reaction mixture was stirred for 22 h under argon. Trimethylamine N-oxide dihydrate (0.60 g, 5.4 mmol) was added and the mixture was heated to reflux overnight and diluted with ether (50 mL). The organic layer was washed with brine (×3), dried (MgSO4), filtered, and evaporated. The crude product was purified by flash chromatography (silica, heptane/ethyl acetate 3:1) to give the title compound as an colorless oil (0.24 g, 62%).

$^1$H NMR (CDCl$_3$, 600 MHz): δ1.17 (t, 3H, J=7 Hz), 1.22 (t, 3H, J=7 Hz), 2.84 (t, 2H, J=7 Hz), 2.99 (m, 2H), 3.36 (dq, 1H, J=7 and 9 Hz), 3.60 (dq, 1H, J=7 and 9 Hz), 3.84 (m, 1H), 4.00 (t, 2H, J=7 Hz), 4.17 (q, 2H, J=7 Hz), 7.14 (dm, 2H, J=8 Hz), 7.19 (dm, 2H, J=8 Hz). $^{13}$C NMR (CDCl$_3$, 75 MHz): δ 14.2, 15.1, 38.8, 38.9, 60.8, 63.6, 66.1, 80.1, 128.7, 129.4, 135.1, 136.6, 172.3.

d) Ethyl(2S)-2-ethoxy-3-[4-(2-{4-[(methylsulfonyl)oxy]phenoxy}ethyl)phenyl]-propanoate A solution of cyanomethylenetri-N-butylphosphorane (0.663 g, 2.75 mmol) in THF (1.5 mL) was added to a solution of ethyl(2S)-2-ethoxy-3-[4-(2-hydroxyethyl)phenyl]-propanoate (0.244 g, 0.92 mmol) and 4-hydroxyphenyl methanesulfonate (0.172 g, 0.92 mmol) in THF (1.5 mL).

The reaction mixture was heated at 150° C. in a microwave oven for 10 minutes. The solvent was removed under reduced pressure. The crude product was purified by flash chromatography (silica, heptane/ethyl acetate 3:1 as the mobile phase) affording 0.167 g (42%) of the title compound.

$^1$H NMR (CDCl$_3$, 400 MHz): 1.17 (t, 3H, J=7 Hz), 1.21 (t, 3H, J=7 Hz), 2.99 (m, 2H), 3.06 (t, 2H, J=7 Hz), 3.10 (s, 3H), 3.36 (dq, 1H, J=7 and 9 Hz), 3.61 (dq, 1H, J=7 and 9 Hz), 4.01 (m, 1H), 4.10-4.20 (m 4H), 6.89 (dm, 2H), 7.18 (dm, 2H), 7.19 (bs, 4H). $^{13}$C NMR (CDCl$_3$, 75 MHz): 14.2, 15.0, 35.2, 36.9, 38.8, 60.7, 66.1, 69.0, 80.0, 115.3, 122.8, 128.6, 129.3, 135.2, 136.0, 142.4, 157.5, 172.2.

e) (2S)-2-Ethoxy-3-[4-(2-{4-[(methylsulfonyl)oxy]phenoxy}ethyl)phenyl]propanoic acid Lithium hydroxide (27 mg, 1.15 mmol) was added to a solution of ethyl(2S)-2-ethoxy-3-[4-(2-{4-[(methylsulfonyl)oxy]phenoxy}ethyl)phenyl]propanoate (167 mg, 0.38 mmol) in THF/water 4:1 (5 mL). The reaction mixture was stirred at room temperature overnight and 1 M HCl (2 mL) was added. The THF was removed under reduced pressure. The aqueous phase was diluted with water and extracted three times with $CH_2Cl_2$ in a Phase Separator. The combined organic layers were evaporated. The residue was purified by preparative HPLC to give the product as a colorless oil (129 mg, 83%).

$^1$H NMR (CD$_3$OD, 500 MHz): δ 1.08 (t, 3H, J=7 Hz), 2.86 (dd, 1H, J=9 and 14 Hz), 2.96-3.02 (m, 3H), 3.12 (s, 3H), 3.27 (dq, 1H, J=7 and 9 Hz), 3.57 (dq, 1H, J=7 and 9 Hz), 3.93 (dd, 1H, J=4 and 9 Hz), 4.12 (t, 2H, J=7 Hz), 6.90 (dm, 2H, J=9 Hz), 7.16-7.22 (m, 6H). $^{13}$C NMR(CD$_3$OD, 100 MHz): δ 15.3, 36.2, 37.1, 40.1, 66.7, 70.3, 82.5, 116.5, 124.2, 129.8, 130.5, 137.5, 137.7, 144.3, 159.2, 178.2.

The term a phenyl $C_{1-6}$alkyl group as used in this specification means that this group is attached to the rest of the molecule by the alkyl group, for example benzyl.

Biological Activity

The compounds of the invention were tested in the assays described in WO03/051821. The compounds of formula I have affinity PPARα and PPARγ. The compounds of formula I are selected because of their superior PPAR alpha/gamma profile in vitro and/or higher affinity and/or better in vivo efficacy. The compounds also have a better selectivity profile, which is expected to improve in vivo safety.

In addition the compounds of the present invention may have improved DMPK (Drug Metabolism and Pharmacokinetic) properties, for example improved metabolic stability in vitro or bioavailability. The compounds also have an improved solubility and/or a promising toxicological profile.

The invention claimed is:

1. A compound of formula I

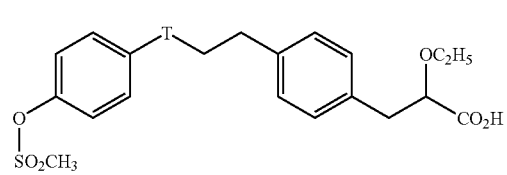

wherein T represents O, S or NR and wherein R represents a H, a $C_{1-6}$alkyl group or a phenyl $C_{1-6}$alkyl group and pharmaceutically acceptable salts thereof.

2. The compound according to claim 1 which is (2S)-2-ethoxy-3-[4-(2-{4-[(methylsulfonyl)oxy]phenoxy}ethyl)phenyl]propanoic acid.

3. A pharmaceutical formulation comprising a compound according to claim 1 or claim 2 in admixture with a pharmaceutically acceptable adjuvant, diluent and/or carrier.

4. A method of treating lipid disorders (dyslipidemia) whether or not associated with insulin resistance comprising the administration of a compound according to claim 1 or claim 2 to a mammal in need thereof.

5. A method of treating type 2 diabetes comprising the administration of an effective amount of a compound of formula I according to claim 1 or claim 2 to a mammal in need thereof.

6. A process for preparing a compound of formula I according to claim 1 comprising reacting a compound of formula II

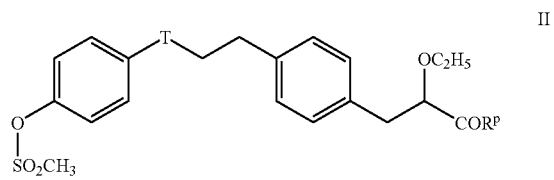

in which T is as defined in claim 1 and $R^p$ represents a protecting group for carboxylic hydroxy group with a de-protecting reagent.

7. A prodrug of a compound of formula I according to claim 1 wherein the prodrug is an in vivo hydrolysable (or cleavable) ester of the carboxylic acid group in the compound of formula (I).

* * * * *